(12) United States Patent
Jothimurugesan et al.

(10) Patent No.: US 8,802,741 B1
(45) Date of Patent: Aug. 12, 2014

(54) HYBRID FISCHER-TROPSCH CATALYSTS AND PROCESSES FOR USE

(71) Applicants: Kandaswamy Jothimurugesan, Hercules, CA (US); Robert James Saxton, Pleasanton, CA (US)

(72) Inventors: Kandaswamy Jothimurugesan, Hercules, CA (US); Robert James Saxton, Pleasanton, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 90 days.

(21) Appl. No.: 13/750,089

(22) Filed: Jan. 25, 2013

(51) Int. Cl.
*C07C 27/00* (2006.01)
*C07C 1/04* (2006.01)
*B01J 29/76* (2006.01)

(52) U.S. Cl.
CPC ........... *C07C 1/0435* (2013.01); *B01J 29/7661* (2013.01)
USPC .......................................... 518/715; 518/700

(58) Field of Classification Search
CPC ...... B01J 29/7661; C07C 1/0435; C07C 9/00; C10G 2/332; C10G 2/334; C10G 2300/1022
USPC .................................. 518/700, 715
See application file for complete search history.

(56) References Cited

U.S. PATENT DOCUMENTS

| 4,906,671 A | 3/1990 | Haag et al. |
| 7,943,674 B1 | 5/2011 | Kibby et al. |
| 8,216,963 B2 | 7/2012 | Kibby et al. |
| 8,263,523 B2 | 9/2012 | Haas et al. |

FOREIGN PATENT DOCUMENTS

EP    0148048    7/1985

OTHER PUBLICATIONS

U.S. Appl. No. 13/603,743, "Improved Hybrid Fischer-Tropsch Catalysts and Processes For Use Thereof," filed Sep. 5, 2012.
U.S. Appl. No. 13/031,341, zeolite supported cobalt hybrid F-T catalyst, filed Feb. 21, 2011.

*Primary Examiner* — Jafar Parsa
(74) *Attorney, Agent, or Firm* — Karen R. DiDomenicis

(57) ABSTRACT

Disclosed are hybrid Fischer-Tropsch catalysts containing cobalt and ZSM-48 zeolite. The hybrid Fischer-Tropsch catalysts can contain cobalt deposited on ZSM-48 extrudate supports. Alternatively, the Fischer-Tropsch catalysts can contain cobalt deposited on supports mixed with ZSM-48 particles. It has surprisingly been found that the use of hybrid Fischer-Tropsch catalysts containing ZSM-48 zeolite in synthesis gas conversion reactions results in improved $C_{5+}$ productivity and catalyst activity, as well as a desirable product distribution including low formation of methane and $C_{21+}$.

13 Claims, No Drawings

HYBRID FISCHER-TROPSCH CATALYSTS AND PROCESSES FOR USE

FIELD

The present disclosure relates to improved hybrid synthesis gas conversion catalysts containing a Fischer-Tropsch component and an acidic zeolite component. The present disclosure further relates to the use of the catalysts in synthesis gas conversion processes to produce liquid hydrocarbon fuels.

BACKGROUND

Fischer-Tropsch synthesis is an effective process for converting synthesis gas containing hydrogen and carbon monoxide, also referred to as syngas, to liquid hydrocarbon fuels. It is well known that Fischer-Tropsch synthesis involves a polymerization reaction beginning with a methylene intermediate to produce a wide distribution of hydrocarbons ranging from light gases to solid wax. Hybrid Fischer-Tropsch catalysts, also referred to interchangeably as "hybrid FT catalysts" or "HFT catalysts," have been developed containing both a Fischer-Tropsch synthesis component, e.g. cobalt, and an acidic zeolite component which have been found to be capable of limiting chain growth in the polymerization reaction to provide a more desirable product distribution.

Challenges have been encountered in hybrid Fischer-Tropsch catalysts containing cobalt as a result of the strong interaction between the cobalt and the zeolite. These may include lower than desired catalytic activity, lower than desired degree of cobalt reduction and undesirably high methane selectivity. For example, the activity of some hybrid Fischer-Tropsch synthesis catalysts which have been reported is about 0.2 g of $C_{5+}/g_{cat}/h$ (U.S. Pat. Nos. 7,973,087; 7,973,086; 7,943,674; and 7,825,164). Generally, it is preferred that the activity of a catalyst be higher.

Another challenge in the development of improved hybrid Fischer-Tropsch catalysts is the development of catalysts which are active, stable and provide high $C_{5+}$ productivity. There remains a need for hybrid Fischer-Tropsch catalysts with improved catalytic activity which provides improved productivity in a desired range of product distribution, i.e., $C_{5+}$.

SUMMARY

In one aspect, a method is provided for performing a Fischer-Tropsch synthesis gas conversion reaction. The method includes contacting a hybrid Fischer-Tropsch catalyst comprising a Fischer-Tropsch metal component selected from cobalt, iron and ruthenium and a ZSM-48 zeolite component with synthesis gas comprising hydrogen and carbon monoxide at a ratio of hydrogen to carbon monoxide of from 1 to 3 at a temperature of from 180 to 280° C. and a pressure of from 5 to 30 atmospheres to yield a hydrocarbon product containing less than 8 weight % $C_{21+}$ and at least 60 weight % $C_{5+}$ at a $C_{5+}$ productivity of at least 0.25 $mLC_{5+}/g_{cat}/h$.

In another aspect, a method is provided for performing a Fischer-Tropsch synthesis gas conversion reaction, including contacting a hybrid Fischer-Tropsch catalyst comprising a Fischer-Tropsch metal component selected from cobalt, iron and ruthenium and a ZSM-48 zeolite component with synthesis gas comprising hydrogen and carbon monoxide at a ratio of hydrogen to carbon monoxide of from 1 to 3 at a temperature of from 180 to 280° C. and a pressure of from 5 to 30 atmospheres to yield a hydrocarbon product containing less than 8 weight % $C_{21+}$ and at least 60 weight % $C_{5+}$ at a $C_{5+}$ productivity of at least 50% greater than an equivalent hybrid Fischer-Tropsch catalyst containing ZSM-5 zeolite rather than ZSM-48.

In another aspect, a method is provided for performing a Fischer-Tropsch synthesis gas conversion reaction, including contacting a hybrid Fischer-Tropsch catalyst comprising a Fischer-Tropsch metal component selected from cobalt, iron and ruthenium and a ZSM-48 zeolite component with synthesis gas comprising hydrogen and carbon monoxide at a ratio of hydrogen to carbon monoxide of from 1 to 3 at a temperature of from 180 to 280° C. and a pressure of from 5 to 30 atmospheres to yield a hydrocarbon product containing less than 8 weight % $C_{21+}$ and at least 60 weight % $C_{5+}$ at a $C_{5+}$ productivity of at least 40% greater than an equivalent hybrid Fischer-Tropsch catalyst containing ZSM-12 zeolite rather than ZSM-48.

In another aspect, a hybrid Fischer-Tropsch catalyst is provided which includes from 5 to 45 weight % cobalt and from 55 to 95 weight % ZSM-48 zeolite.

DETAILED DESCRIPTION

Hybrid Fischer-Tropsch catalysts include at least one Fischer-Tropsch component and at least one acidic component. As is known, the presence of an acidic component such as a zeolite enables the hybrid Fischer-Tropsch catalyst to limit the formation of undesirable heavy hydrocarbon components, such as $C_{21+}$ wax. In one embodiment, the Fischer-Tropsch component can be deposited onto a support containing the zeolite. In another embodiment, the Fischer-Tropsch component and the zeolite component can be separate mixed particles.

The Fischer-Tropsch component may also be referred to herein as the "Fischer-Tropsch metal," "synthesis gas conversion component" or "syngas conversion component." The Fischer-Tropsch component includes a Group VIII of the Periodic Table metal component, preferably cobalt, iron and/or ruthenium. References to the Periodic Table and groups thereof used herein refer to the IUPAC version of the Periodic Table of Elements described in the 68th Edition of the Handbook of Chemistry and Physics (CPC Press). The optimum amount of catalytically active metal present depends inter alia on the specific catalytically active metal. Typically, the amount of cobalt present in the catalyst may range from 1 to 100 parts by weight per 100 parts by weight of support material, preferably from 10 to 50 parts by weight per 100 parts by weight of support material.

The catalytically active Fischer-Tropsch component may be present in the catalyst together with one or more metal promoters or co-catalysts. The promoters may be present as metals or as metal oxide, depending upon the particular promoter concerned. Suitable promoters include metals or oxides of metals from Groups IA, IB, IVB, VB, VIB and/or VIIB of the Periodic Table, lanthanides and/or the actinides or oxides of the lanthanides and/or the actinides. As an alternative or in addition to the metal oxide promoter, the catalyst may comprise a metal promoter selected from Groups VIIB and/or VIII of the Periodic Table. In some embodiments, the Fischer-Tropsch component further comprises a cobalt reduction promoter selected from the group consisting of platinum, ruthenium, rhenium, silver and combinations thereof.

According to the present disclosure, the acidic zeolite component of the hybrid Fischer-Tropsch catalyst is advantageously ZSM-48. The use of ZSM-48 has been found to provide a surprisingly high level of activity and productivity.

ZSM-48 has a chemical formula of Si48O96 and a framework structure of *MRE designated by the Structure Commission of the International Zeolite Association (IZA-SC) wherein the * indicates that the structure is disordered. It has a framework density of 19.9 T/1000 Å3. ZSM-48 has one-dimensional channels. The ZSM-48 zeolite advantageously is characterized by having a SiO2/Al2O3 ratio of from 60 to 190, even from 60 to 120. Further details on the structure of ZSM-48 can be found at Ch. Baerlocher and L. B. McCusker, Database of Zeolite Structures: http://www.iza-structure.org/databases/ and Schlenker, J. L. Rohrbaugh, W. J., Chu, P., Valyocsik, E. W. and Kokotailo, G. T. Zeolites, 5, 355-358 (1985).

The amount of acidic component used in the catalyst can be suitably varied to obtain the desired product. For instance, if the amount of acidic component is too low, there may be insufficient cracking to remove a desired amount of wax; whereas if too much acidic component is used, there may be excessive cracking and the resulting product may be lighter than desired.

In one embodiment, the hybrid Fischer-Tropsch catalyst can contain from 55 to 95 weight % ZSM-48 zeolite extrudate impregnated with from 5 to 45 weight % cobalt. In another embodiment, the hybrid Fischer-Tropsch catalyst can contain from 70 to 90 weight % ZSM-48 zeolite extrudate impregnated with from 10 to 30 wt % cobalt.

In one embodiment, the hybrid Fischer-Tropsch catalyst extrudate has a BET surface area of greater than 90 $m^2/g$. In another embodiment, the hybrid Fischer-Tropsch catalyst extrudate has a BET surface area of from 100 to 300 $m^2/g$.

The ZSM-48 zeolite component may further contain a promoter such as platinum, ruthenium, rhenium, silver, palladium, nickel, rhodium, iridium or combinations thereof.

In addition to the zeolite component, the supports of the hybrid Fischer-Tropsch catalysts can further include a binder material. Suitable binder materials for use in the support include alumina, silica, titania, zirconia and combinations thereof. The binder can represent less than 40 weight % of the hybrid Fischer-Tropsch catalyst. The supports are advantageously formed by mixing the zeolite component with the binder material and extruding the mixture to form ZSM-48 extrudates. In embodiments in which the Fischer-Tropsch component and the zeolite component are separate mixed particles, the cobalt can be deposited onto one of the above listed binder materials.

The method employed to deposit the Fischer-Tropsch component on an extrudate support involves an impregnation technique using aqueous or non-aqueous solution containing a soluble cobalt salt in a suitable solvent and, if desired, a soluble promoter metal salt, e.g., platinum salt, in order to achieve the necessary metal loading and distribution required to provide a highly selective and active hybrid synthesis gas conversion catalyst.

Initially, the support can be treated by oxidative calcination at a temperature in the range of from 450° to 900° C., for example, from 600° to 750° C., to remove water and any organics from the support.

Suitable solvents include, for example, water, ketones, such as acetone, butanone (methyl ethyl ketone); the lower alcohols, e.g., methanol, ethanol, propanol and the like; amides, such as dimethyl formamide; amines, such as butylamine; ethers, such as diethylether and tetrahydrofuran; hydrocarbons, such as pentane and hexane; and mixtures of the foregoing solvents. In one embodiment, the solvent is ethanol, for use with cobalt nitrate.

Suitable cobalt salts include, for example, cobalt nitrate, cobalt acetate, cobalt carbonyl, cobalt acetylacetonate, and the like. Likewise, any suitable platinum salt, such as chloroplatinic acid hexahydrate, tetraammineplatinum nitrate, tetraamminoplatinum hydroxide or the like can be used. In one embodiment, tetraammineplatinum nitrate is used. In general, any metal salt which is soluble in the suitable solvent and will not have a poisonous effect on the metal catalyst or on the acid sites of the ZSM-48 can be used.

The calcined support is then impregnated in a dehydrated state with the aqueous or non-aqueous solvent solution of the metal salts. Care should be taken so that the calcined support is not unduly exposed to atmospheric humidity so as to become rehydrated.

Any suitable impregnation technique can be employed including techniques well known to those skilled in the art so as to distend the catalytic metals in a uniform thin layer on the catalyst support. For example, the cobalt along with the oxide promoter can be deposited on the support material by the "incipient wetness" technique. Such technique is well known and requires that the volume of aqueous or non-aqueous solution be predetermined so as to provide the minimum volume which will just wet the entire surface of the support, with no excess liquid. Alternatively, the excess solution technique can be used if desired. If the excess solution technique is used, then the excess solvent present, e.g., ethanol is merely removed by evaporation.

Next, the aqueous or non-aqueous solution and support are stirred while evaporating the solvent at a temperature of from 25° to 50° C. until "dryness."

The impregnated catalyst is slowly dried at a temperature of from 110° to 120° C. for a period of about 1 hour to spread the metals over the entire support. The drying step is conducted at a very slow rate in air.

The dried catalyst may be reduced directly in hydrogen or it may be calcined first. In the case of impregnation with cobalt nitrate, direct reduction can yield a higher cobalt metal dispersion and synthesis activity, but reduction of nitrates is difficult to control; calcination before reduction may be preferred for large scale preparations. A single calcination step to decompose nitrates may be preferred if multiple impregnations are needed to provide the desired metal loading. Reduction in hydrogen requires a prior purge with inert gas, a subsequent purge with inert gas and a passivation step in addition to the reduction itself, as described later as part of the reduction-oxidation-reduction (ROR) activation. However, impregnation of cobalt carbonyl is preferably carried out in a dry, oxygen-free atmosphere and decomposed directly, then passivated.

The dried catalyst is calcined by heating slowly in flowing air, for example 10 cc/gram/minute, to a temperature in the range of from 200° to 350° C., for example, from 250° to 300° C., that is sufficient to decompose the metal salts and fix the metals. The aforesaid drying and calcination steps can be done separately or can be combined. Calcination should be conducted by using a slow heating rate of, for example, 0.5° to 3° C. per minute or from 0.5° to 1° C. per minute and the catalyst should be held at the maximum temperature for a period of from 1 to 20 hours, for example, for 2 hours.

The foregoing impregnation steps are repeated with additional solutions in order to obtain the desired metal loading. Platinum and other promoter metal oxides are conveniently added together with cobalt, but they may be added in other impregnation steps, separately or in combination, either before, after, or between impregnations of cobalt.

The hybrid FT catalyst prepared according to any of the foregoing methods can optionally be further activated prior to use in a synthesis gas conversion process by either reduction in hydrogen or a reduction-oxidation-reduction (ROR) treatment. The reduction or ROR activation treatment is conducted at a temperature considerably below 500° C. in order to achieve the desired increase in activity and selectivity of the hybrid FT catalyst. Temperatures of 500° C. or above reduce activity and liquid hydrocarbon selectivity of the catalyst. Suitable reduction or ROR activation temperatures are below 500° C., even below 450° C. and even at or below 400° C. Thus, ranges of from 100° C. or 150° C. to 450° C., for example, from 250° C. to 400° C., are suitable for the reduction steps. The oxidation step should be limited to from 200° C. to 300° C. These activation steps are conducted while heating at a rate of from 0.1° C. to 5° C., for example, from 0.10° C. to 2° C.

The catalyst can be slowly reduced in the presence of hydrogen. If the catalyst has been calcined after each impregnation, to decompose nitrates or other salts, then the reduction may be performed in one step, after an inert gas purge, with heating in a single temperature ramp (e.g., 1° C./min.) to the maximum temperature and held at that temperature, from 250° C. or 300° C. to 450° C., for example, from 350° C. to 400° C., for a hold time of from 6 to 65 hours, for example, from 16 to 24 hours. Pure hydrogen is preferred in the first reduction step. If nitrates are still present, the reduction is best conducted in two steps wherein the first reduction heating step is carried out at a slow heating rate of no more than 5° C. per minute, for example, from 0.1° C. to 1° C. per minute up to a maximum hold temperature of from 200° C. to 300° C., for example, from 200° C. to 250° C., for a hold time of from 6 to 24 hours, for example, from 16 to 24 hours under ambient pressure conditions. In the second treating step of the first reduction, the catalyst can be heated at from 0.5° C. to 3° C. per minute, for example, from 0.1° C. to 1° C. per minute to a maximum hold temperature of from 250° C. or 300° C. up to 450° C., for example, from 350° C. to 400° C. for a hold time of from 6 hours to 65 hours, for example, from 16 to 24 hours. Although pure hydrogen is preferred for these reduction steps, a mixture of hydrogen and nitrogen can be used.

Thus, the reduction may involve the use of a mixture of hydrogen and nitrogen at 100° C. for one hour; increasing the temperature 0.5° C. per minute until a temperature of 200° C.; holding that temperature for approximately 30 minutes; and then increasing the temperature 1° C. per minute until a temperature of 350° C. is reached and then continuing the reduction for approximately 16 hours. Reduction can be conducted sufficiently slowly and the flow of the reducing gas maintained sufficiently high to maintain the partial pressure of water in the offgas below 1%, to avoid excessive steaming of the outlet end of the catalyst bed. Before and after all reductions, the catalyst can be purged in an inert gas such as nitrogen, argon or helium.

The reduced catalyst can be passivated at ambient temperature (25° C. to 35° C.) by flowing diluted air over the catalyst sufficiently slowly so that a controlled exotherm of no larger than +50° C. passes through the catalyst bed. After passivation, the catalyst is heated slowly in diluted air to a temperature of from 300° C. to 350° C. in the same manner as previously described in connection with calcination of the catalyst.

The temperature of the exotherm during the oxidation step can be less than 100° C., and will be 50° C. to 60° C. if the flow rate and/or the oxygen concentration are dilute enough.

Next, the reoxidized catalyst is slowly reduced again in the presence of hydrogen, in the same manner as previously described in connection with the initial reduction of the catalyst. Since nitrates are no longer present, this reduction may be accomplished in a single temperature ramp and held, as described above for the reduction of the calcined catalysts.

The hybrid Fischer-Tropsch catalyst of the present disclosure can be utilized in a process the synthesis gas conversion in which a synthesis gas feed containing hydrogen and carbon monoxide is contacted in a reactor with the hybrid Fischer-Tropsch catalyst to produce a hydrocarbon product containing at least 60 wt % $C_{5+}$ hydrocarbons. The synthesis gas feed can have a $H_2$/CO ratio between 1 and 3. The reaction can occur at a temperature from 180 to 280° C., a pressure from 5 to 30 atmospheres, and a gaseous hourly space velocity less than 20,000 volumes of gas per volume of catalyst per hour. In one embodiment, the $C_{5+}$ productivity of the process is advantageously at least 0.25 mL$C_{5+}$/$g_{cat}$/h (milliliters of $C_{5+}$ per grams of catalyst per hour), even at least 0.30 mL$C_{5+}$/$g_{cat}$/h, and even at least 0.35 mL$C_{5+}$/$g_{cat}$/h. It has been found that the $C_{5+}$ productivity of the process is at least 50% greater, even at least 80% greater, than an equivalent hybrid Fischer-Tropsch catalyst containing ZSM-5 zeolite rather than ZSM-48. It has further been found that the $C_{5+}$ productivity of the process is at least 40% greater, even at least 55% greater, than an equivalent hybrid Fischer-Tropsch catalyst containing ZSM-12 zeolite rather than ZSM-48.

In one embodiment, the resulting hydrocarbon product further contains:
    0-20 wt % $CH_4$;
    0-16 wt % $C_2$-$C_4$;
    60-80 wt % $C_{5+}$; and
    0-8 wt % $C_{21+}$.

The reactor type can be selected from any reactor type known for use in a Fischer-Tropsch synthesis process, including, but not limited to, multi-tubular fixed bed reactors, circulating fluidized bed reactors, fixed fluidized bed reactors, compact heat exchange reactors and microchannel reactors. When a multi-tubular fixed bed reactor is used, the particle size of the hybrid Fischer-Tropsch catalyst can be between 1 and 3 mm. When a circulating or fixed fluidized bed reactor is used, the particle size can be between 35 and 175 µm. When a compact heat exchange reactor or microchannel reactor is used, the particle size can be between 10 and 250 µm.

Analytical Methods

BET surface area and pore volume of catalyst samples were determined from nitrogen adsorption/desorption isotherms measured at −196° C. using a Tristar analyzer available from Micromeritics Instrument Corporation (Norcross, Ga.). Prior to gas adsorption measurements, the catalyst samples were degassed at 190° C. for 4 hours. The total pore volume (TPV) was calculated at a relative pressure of approximately 0.99.

Metal dispersion and average particle diameter were measured by hydrogen chemisorption using an AutoChem 2900 analyzer available from Micromeritics Instrument Corporation (Norcross, Ga.). The fraction of surface cobalt on the catalysts was measured using $H_2$ temperature programmed desorption (TPD). Samples (0.25 g) were heated to 350° C. in $H_2$ at 1° C. min$^{-1}$ and held for 3 hours then cooled to 30° C. Then a flow of argon was used to purge the samples before heating to 350° C. at 20° C. min$^{-1}$. Hydrogen desorption was monitored using a thermal conductivity detector. TPD were repeated after oxidizing samples in 10% $O_2$/He and a second reduction in pure hydrogen. Dispersions were calculated relative to the cobalt concentration in each sample.

Average crystallite size (diameter) of cobalt in nanometers was estimated by assuming a spherical geometry of reduced cobalt. The fraction of reduced cobalt was measured by dehydrating as-prepared materials, prior to reduction, at 350° C., then cooling to room temperature and reducing in 5% $H_2$/Ar at a heating rate of 5° C. min$^{-1}$ to 350° C. Catalyst reducibility during H$_2$ TPR was measured using TGA, and weight losses were assumed to be from cobalt oxide reduction in order to calculate O/Co stoichiometric ratios. The fractional reducibility was calculated by assuming the complete reduction of Co$_3$O$_4$ to Co metal, calculated using the equation below:

$$d = 96.2 * (\text{Co Fractional Reduction}) / \% \text{ Dispersion}$$

EXAMPLES

Example 1

Preparation of Catalyst Extrudates Comprising 10 Weight % Co-0.25 Weight % Ru Supported on 80 Weight % ZSM-48 and 20 Weight % Alumina ZSM-48 zeolite powder having a SiO$_2$/Al$_2$O$_3$ ratio of 120 was obtained from Sud-Chemie, Inc. (Munich, Germany). 96 g of the ZSM-48 powder and 24 g of catapal B alumina powder were added to a mixer and mixed for 10 minutes. 60 g of deionized water and 4.5 g of nitric acid were added to the mixed powder and mixed for 10 minutes. The mixture was then transferred to a 1 inch (2.54 cm) BB gun extruder available from The Bonnot Company (Uniontown, Ohio) and extruded through a dieplate containing thirty 1/16 inch (0.16 cm) holes. The ZSM-48 extrudates were dried first at 70° C. for 2 h, then at 120° C. for 2 h and finally calcined in flowing air at 600° C. for 2 h.

A catalyst containing 10% Co-0.25% Ru on 1/16 inch (0.16 cm) alumina-bound ZSM-48 extrudates was prepared in a single step using non-aqueous impregnation. The ZSM-48 extrudates prepared as above were used. First, 0.3396 g of ruthenium acetylacetonate (available from Alfa Aesar, Ward Hill, Mass.) was dissolved in 40 g of acetone. Second, 16.59 g of cobalt(II) nitrate hexahydrate (available from Sigma-Aldrich, St. Louis, Mo.) was dissolved in 80 g of acetone. The two solutions were then mixed together and added to the 30 g of dry alumina-bound ZSM-48 extrudates. The solvent was removed in a rotary evaporator under vacuum by heating slowly to 45° C. The vacuum-dried material was then further dried in air in an oven at 120° C. overnight. The dried catalyst extrudates were then calcined at 300° C. for 2 hours in a muffle furnace. The properties of the ZSM-48 zeolite powder and the catalyst extrudates are shown in Table 1.

TABLE 1

| Catalyst Composition | Micropore Area, m$^2$/g | External Surface Area, m$^2$/g | BET Surface Area, m$^2$/g | Pore Volume cc/g | Micropore volume cc/g | Dispersion, % | Average Particle Diameter, nm |
|---|---|---|---|---|---|---|---|
| ZSM-48 | 136.56 | 120.66 | 257.22 | 0.4192 | 0.0635 | na | na |
| 10% Co-0.25 Ru/ (80% ZSM-48 + 20% Al$_2$O$_3$) | 43.57 | 98.27 | 141.8 | 0.2670 | 0.0200 | 16.1 | 6.2 |

Catalyst Activation

Ten grams of catalyst prepared as described above was charged to a glass tube reactor. The reactor was placed in a muffle furnace with upward gas flow. The tube was purged first with nitrogen gas at ambient temperature, after which time the gas feed was changed to pure hydrogen with a flow rate of 750 sccm. The temperature to the reactor was increased to 350° C. at a rate of 1° C./minute and then held at that temperature for six hours. After this time, the gas feed was switched to nitrogen to purge the system and the unit was then cooled to ambient temperature. Then a gas mixture of 1 volume % O$_2$/N$_2$ was passed up through the catalyst bed at 750 sccm for 10 hours to passivate the catalyst. No heating was applied, but the oxygen chemisorption and partial oxidation exotherm caused a momentary temperature rise. After 10 hours, the gas feed was changed to pure air, the flow rate was lowered to 200 sccm and the temperature was raised to 300° C. at a rate of 1° C./minute and then kept at 300° C. for two hours. At this point, the catalyst was cooled to ambient temperature and discharged from the glass tube reactor. It was transferred to a 316-SS tube reactor of 0.51 in (1.3 cm) inner diameter and placed in a clam-shell furnace. The catalyst bed was flushed with a downward flow of helium for a period of two hours, after which time the gas feed was switched to pure hydrogen at a flow rate of 500 sccm. The temperature was slowly raised to 120° C. at a temperature interval of 1° C./minute, held there for a period of one hour, then raised to 250° C. at a temperature interval of 1° C./minute and held at that temperature for 10 hours. After this time, the catalyst bed was cooled to 180° C. while remaining under a flow of pure hydrogen gas. All flows were directed downward.

Fischer-Tropsch Activity

Catalysts prepared and activated as described above were subjected to a synthesis run in which the catalyst was contacted with syngas containing hydrogen and carbon monoxide. Experimental conditions and results are given in Table 2.

TABLE 2

| | Experiment No. | | |
|---|---|---|---|
| | 1 | 2 | 3 |
| TOS, h | 77 | 116 | 146 |
| Yield Time, h | 25.5 | 39.3 | 30.5 |
| Temperature, ° C. | 220.0 | 220.0 | 220.0 |
| Pressure, atm | 20 | 20 | 20 |
| H$_2$/CO Fresh Feed | 2.00 | 2.00 | 2.00 |
| H$_2$ Conv(mol %). | 45.2% | 44.1% | 43.3% |
| CO Conv(mol %). | 39.10% | 37.90% | 37.60% |
| Rate, gCH$_2$/g/h | 0.41 | 0.40 | 0.39 |
| Rate, mLC$_5$$^+$/g/h | 0.35 | 0.35 | 0.34 |
| CO$_2$, wt % | 1.10% | 0.90% | 1.00% |
| CH$_4$, wt % | 18.8% | 18.6% | 18.8% |
| C$_2$, wt % | 2.1% | 2.0% | 2.0% |
| C$_3$, wt % | 7.9% | 7.8% | 7.8% |
| C$_4$, wt % | 5.2% | 5.2% | 4.9% |
| C$_5$$^+$, wt % | 64.8% | 65.5% | 65.5% |
| C$_{21}$$^+$, wt % | 5.1% | 7.2% | 7.4% |

TABLE 2-continued

|  | Experiment No. | | |
| --- | --- | --- | --- |
|  | 1 | 2 | 3 |
| C1-C3, wt % | 28.8% | 28.4% | 28.6% |
| $C_2^=/C_2$, mol % | 2.9% | 2.1% | 3.1% |
| $C_3^=/C_3$, mol % | 29.2% | 28.4% | 27.7% |
| $C_4^=/C_4$, mol % | 31.4% | 31.9% | 30.4% |
| DOB, mol % | 5.1% | 5.7% | 5.1% |

It can be seen from the results in Table 2 that the hybrid Fischer-Tropsch catalyst of the present invention prepared using ZSM-48 zeolite is effective for the conversion of synthesis gas to give a liquid hydrocarbon product substantially free of solid wax under commercially viable process conditions. Further, the yield of C5+ hydrocarbons is above 60%.

Comparative Example 1

Hybrid Catalyst Prepared with ZSM-48 and Hybrid Catalyst Prepared with ZSM-5

A catalyst comprising 10.0% weight Co/0.25% weight Ru on 80% weight ZSM-5 and 20% weight alumina was prepared according to the following procedure. First, ruthenium acetylacetonate was dissolved in acetone. Second, cobalt nitrate was dissolved in acetone. The two solutions were mixed together and then added to 1/16" extrudates of alumina (20 weight % alumina) bound ZSM-5 zeolite (Si/Al=15, obtained from Zeolyst International, Conshohocken, Pa.). After the mixture was stirred for 1 hour at ambient temperature, the solvent was eliminated by rotavaporation. Then the catalyst was dried in an oven at 120° C. overnight and finally calcined at 300° C. for 2 hours in a muffle furnace.

The data presented in Tables 2 and 3 provide a comparison of hybrid, integral catalysts prepared with ZSM-48 and ZSM-5 zeolites. It can be seen from Tables 2 and 3 that a hybrid, integral catalyst prepared with ZSM-48 surprisingly results in a higher yield of desired $C_{5+}$ product while producing lower yields of undesired light gases with good conversion of synthesis gas. In fact, the $C_{5+}$ productivity of the process using the hybrid catalyst prepared with ZSM-48 (Example 1) is shown to be at least 80% greater than the equivalent hybrid Fischer-Tropsch catalyst containing a ZSM-5 zeolite rather than ZSM-48 (Comparative Example 1). By "equivalent hybrid Fischer-Tropsch catalyst containing ZSM-5 zeolite rather than ZSM-48" is meant that the catalysts are prepared in the same manner using the same weight percentages of the catalyst components and using all identical components other than the zeolite type.

No solid wax was seen for either catalyst under these reaction conditions.

TABLE 3

|  | Hybrid catalyst Prepared with ZSM-48 | Hybrid catalyst Prepared with ZSM-5 |
| --- | --- | --- |
| TOS, h | 77 | 168 |
| Yield Time, h | 25.5 | 41 |
| Temperature, ° C. | 220.0 | 220 |
| Pressure, atm | 20 | 20 |
| $H_2$/CO Fresh Feed | 2.00 | 2 |
| $H_2$ Conv(mol %). % | 45.2 | 27.0 |
| CO Conv(mol %). % | 39.10 | 33.1 |
| Rate, $gCH_2/g/h$ | 0.41 | 0.23 |
| Rate, $mLC_5^+/g/h$ | 0.35 | 0.19 |

TABLE 3-continued

|  | Hybrid catalyst Prepared with ZSM-48 | Hybrid catalyst Prepared with ZSM-5 |
| --- | --- | --- |
| $CO_2$, wt % | 1.10 | 0.6 |
| $CH_4$, wt % | 18.8 | 21.9 |
| $C_2$, wt % | 2.1 | 2.2 |
| $C_3$, wt % | 7.9 | 8.9 |
| $C_4$, wt % | 5.2 | 5.4 |
| $C_5$+, wt % | 64.8 | 61.3 |
| $C_{21}^+$, wt % | 5.1 | 5.1 |
| C1-C3, wt % | 28.8 | 33.0 |
| $C_2^=/C_2$, mol % | 2.9% | 2.5 |
| $C_3^=/C_3$, mol % | 29.2% | 28.3 |
| $C_4^=/C_4$, mol % | 31.4% | 36.9 |
| DOB, mol % | 5.1% | 7.7 |

Comparative Example 2

Hybrid Catalyst Extrudates Prepared with ZSM-48 and Hybrid Catalyst Extrudates Prepared with ZSM-12

A catalyst comprising 10.0% weight Co/0.25% weight Ru on 80% weight ZSM-12 and 20% weight alumina was prepared according to the following procedure. First, ruthenium nitrosyl nitrate was dissolved in acetone. Second, cobalt nitrate was dissolved in acetone. The two solutions were mixed together and then added to 1/16 in (0.16 cm) extrudates of alumina (20 weight % alumina) bound ZSM-12 zeolite (Si/Al=45, obtained from Zeolyst International, Conshohocken, Pa.). After the mixture was stirred for 1 hour at ambient temperature, the solvent was eliminated by rotavaporation. Then the catalyst extrudates were dried in an oven at 120° C. overnight and finally calcined at 300° C. for 2 hours in a muffle furnace.

The data presented in Tables 2 and 4 provide a comparison of hybrid, integral catalysts prepared with ZSM-48 and ZSM-12 zeolite extrudates. It can be seen from Tables 2 and 3 that a hybrid, integral catalyst extrudates prepared with ZSM-48 surprisingly result in a higher yield of desired C5+ product while producing lower yields of undesired light gases with good conversion of synthesis gas. The $C_{5+}$ productivity of the process using the hybrid catalyst prepared with ZSM-48 (Example 1) is shown to be at least 55% greater than the equivalent hybrid Fischer-Tropsch catalyst comprising a ZSM-12 zeolite extrudate impregnated with cobalt (Comparative Example 2). No solid wax was seen for either catalyst under these reaction conditions.

TABLE 4

|  | Hybrid catalyst Prepared with ZSM-48 | Hybrid catalyst Prepared with ZSM-12 |
| --- | --- | --- |
| TOS, h | 77 | 96 |
| Yield Time, h | 25.5 | 25.5 |
| Temperature, ° C. | 220.0 | 220.0 |
| Pressure, atm | 20 | 20 |
| $H_2$/CO Fresh Feed | 2.00 | 2.0 |
| $H_2$ Conv(mol %). | 45.2 | 32.9 |
| CO Conv(mol %). | 39.10 | 26.3 |
| Rate, $gCH_2/g/h$ | 0.41 | 0.28 |
| Rate, $mLC_5^+/g/h$ | 0.35 | 0.22 |
| $CO_2$, wt % | 1.10 | 0.5 |
| $CH_4$, wt % | 18.8 | 24.6 |
| $C_2$, wt % | 2.1 | 2.1 |
| $C_3$, wt % | 7.9 | 8.0 |

TABLE 4-continued

| | Hybrid catalyst Prepared with ZSM-48 | Hybrid catalyst Prepared with ZSM-12 |
|---|---|---|
| $C_4$, wt % | 5.2 | 5.0 |
| $C_5+$, wt % | 64.8 | 59.8 |
| $C_{21}{}^+$, wt % | 5.1 | 5.2 |
| C1-C3, wt % | 28.8 | 34.7 |
| $C_2{}^=/C_2$, mol % | 2.9% | 3.9% |
| $C_3{}^=/C_3$, mol % | 29.2% | 28.4% |
| $C_4{}^=/C_4$, mol % | 31.4% | 29.6% |
| DOB, mol % | 5.1% | 6.4% |

What is claimed is:

1. A method of performing a Fischer-Tropsch synthesis gas conversion reaction, the method comprising:
    a. contacting a hybrid Fischer-Tropsch catalyst comprising a Fischer-Tropsch metal component selected from cobalt, iron and ruthenium and a ZSM-48 zeolite component with synthesis gas comprising hydrogen and carbon monoxide at a ratio of hydrogen to carbon monoxide of from 1 to 3 at a temperature of from 180 to 280° C. and a pressure of from 5 to 30 atmospheres to yield a hydrocarbon product containing less than 8 weight % $C_{21+}$ and at least 60 weight % $C_{5+}$ at a $C_{5+}$ productivity of at least 0.25 $mLC_{5+}/g_{cat}/h$.

2. A method of performing a Fischer-Tropsch synthesis gas conversion reaction, the method comprising:
    a. contacting a hybrid Fischer-Tropsch catalyst comprising a Fischer-Tropsch metal component selected from cobalt, iron and ruthenium and a ZSM-48 zeolite component with synthesis gas comprising hydrogen and carbon monoxide at a ratio of hydrogen to carbon monoxide of from 1 to 3 at a temperature of from 180 to 280° C. and a pressure of from 5 to 30 atmospheres to yield a hydrocarbon product containing less than 8 weight % $C_{21+}$ and at least 60 weight % $C_{5+}$ at a $C_{5+}$ productivity of at least 50% greater than an equivalent hybrid Fischer-Tropsch catalyst containing ZSM-5 zeolite rather than ZSM-48.

3. The method of claim 2, wherein the $C_{5+}$ productivity is at least 80% greater than an equivalent hybrid Fischer-Tropsch catalyst containing ZSM-5 zeolite rather than ZSM-48.

4. A method of performing a Fischer-Tropsch synthesis gas conversion reaction, the method comprising:
    a. contacting a hybrid Fischer-Tropsch catalyst comprising a Fischer-Tropsch metal component selected from cobalt, iron and ruthenium and a ZSM-48 zeolite component with synthesis gas comprising hydrogen and carbon monoxide at a ratio of hydrogen to carbon monoxide of from 1 to 3 at a temperature of from 180 to 280° C. and a pressure of from 5 to 30 atmospheres to yield a hydrocarbon product containing less than 8 weight % $C_{21+}$ and at least 60 weight % $C_{5+}$ at a $C_{5+}$ productivity of at least 40% greater than an equivalent hybrid Fischer-Tropsch catalyst containing ZSM-12 zeolite rather than ZSM-48.

5. The method of claim 4, wherein the $C_{5+}$ productivity of at least 55% greater than an equivalent hybrid Fischer-Tropsch catalyst containing ZSM-12 zeolite rather than ZSM-48.

6. The method of any of claim 1, 2 or 4, wherein the hybrid Fischer-Tropsch catalyst comprises an extrudate comprising a support containing ZSM-48 impregnated with cobalt.

7. The method of any of claim 1, 2 or 4, wherein the hybrid Fischer-Tropsch catalyst comprises a mixture of cobalt deposited onto a support and ZSM-48 particles.

8. The method of claim 1, wherein the hydrocarbon product further contains:
    a. less than 20 weight % methane; and
    b. less than 16 weight % $C_2$-$C_4$.

9. The method of claim 1, wherein the $C_{5+}$ productivity is at least 0.30 $mL_{C5+}/g_{cat}/h$.

10. The method of claim 1, wherein the $C_{5+}$ productivity is at least 0.35 $mL_{C5+}/g_{cat}/h$.

11. The method of claim 1, wherein the hybrid Fischer-Tropsch catalyst comprises from 55 to 95 weight % ZSM-48 zeolite and from 5 to 45 weight % cobalt.

12. The method of claim 1, wherein the hybrid Fischer-Tropsch catalyst comprises from 70 to 90 weight % ZSM-48 zeolite and from 10 to 30 weight % cobalt.

13. The method of claim 1, wherein the ZSM-48 zeolite has a $SiO_2/Al_2O_3$ ratio of from 60 to 190.

* * * * *